United States Patent [19]

Buntain et al.

[11] Patent Number: 4,963,575
[45] Date of Patent: Oct. 16, 1990

[54] DERIVATIVES OF N-PHENYLPYRAZOLES, COMPOSITIONS AND USE

[75] Inventors: Ian G. Buntain; Leslie R. Hatton, both of Chelmsford; David W. Hawkins, Upminster; Christopher J. Pearson, Hertford; David A. Roberts, Mill Hill, all of England

[73] Assignee: May & Baker Ltd., Dagenham, England

[21] Appl. No.: 379,982

[22] Filed: Jul. 14, 1989

[30] Foreign Application Priority Data

Jul. 15, 1988 [GB] United Kingdom ............... 8816915

[51] Int. Cl.$^5$ ................. A01N 43/56; A01N 43/647;
A01N 43/653; C07D 403/04
[52] U.S. Cl. ................................... 514/359; 514/383;
514/397; 514/407; 548/255; 548/266.2;
548/336; 548/374
[58] Field of Search ........... 548/336, 374, 255, 266.2;
514/359, 383, 397, 407

[56] References Cited

U.S. PATENT DOCUMENTS 4,803,215 2/1989 Jensen-Korte et al. ............. 548/374
4,845,089 7/1989 Lindig et al. ....................... 548/374

Primary Examiner—Robert W. Ramsuer
Attorney, Agent, or Firm—Burns, Doane, Swecker & Mathis

[57] ABSTRACT

An N-phenylpyrazole derivative of the formula:

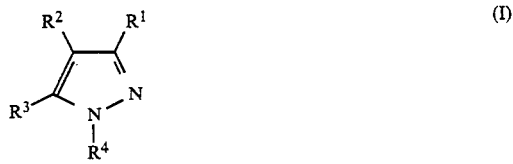

(I)

wherein $R^1$ represents cyano, nitro or halogen;

$R^2$ represents a group $R^5SO_2$, $R^5SO$, or $R^5S$ in which $R^5$ represents alkyl, alkenyl or alkynyl unsubstituted or substituted by halogen;

$R^3$ represents azido or hydrazino, or pyrrol-1-yl, pyrazol-1-yl, imidazol-1-yl, 1,2,4-triazol-4-yl, 1,2,4-triazol-1-yl, 1,2,3-triazol-1-yl, 1,2,3-triazol-2-yl, piperidino, pyrrolidino, morpholino or N-alkylpiperazino, which may be substituted by alkyl or phenyl; and $R^4$ represents phenyl substituted in the 2-position by fluorine, chlorine, bromine or iodine;

in the 4-position by alkyl or alkoxy unsubstituted or substituted by halogen, or fluorine, chlorine, bromine or iodine; and unsubstituted or substituted in the 6-position by fluorine, chlorine, bromine or iodine and pesticidally acceptable acid addition salts thereof possess arthropodicidal, nematocidal, anthelmintic and antiprotozoal activity.

9 Claims, No Drawings

DERIVATIVES OF N-PHENYLPYRAZOLES, COMPOSITIONS AND USE

This invention relates to N-phenylpyrazole derivatives, to compositions containing them and to the use of N-phenylpyrazole derivatives against arthropod, plant nematode, helminth and protozoan pests.

The present invention provides N-phenylpyrazole derivatives of the general formula (I) depicted hereinafter wherein $R^1$ represents a cyano or nitro group, a halogen, i.e. fluorine, chlorine, bromine or iodine, atom; $R^2$ represents a group $R^5SO_2$, $R^5SO$, or $R^5S$ in which $R^5$ represents a straight or branched chain alkyl, alkenyl or alkynyl group containing up to 4 carbon atoms which may be unsubstituted or substituted by one or more halogen atoms which may be the same or different; $R^3$ represents an azido or hydrazino group or preferably represents a group Het selected from pyrrol-1-yl, pyrazol-1-yl, imidazol-1-yl, 1,2,4-triazol-4-yl, 1,2,4-triazol-1-yl, 1,2,3-triazol-1-yl, 1,2,3-triazol-2-yl, piperidino, pyrrolidino, morpholino and N-alkylpiperazino, which may be substituted by alkyl or phenyl groups; and $R^4$ represents a phenyl group substituted in the 2-position by a fluorine, chlorine, bromine or iodine atom; in the 4-position by a straight or branched chain alkyl or alkoxy group containing from 1 to 4 carbon atoms which may be unsubstituted or substituted by one or more halogen atoms which may be the same or different (the trifluoromethyl and trifluoromethoxy groups are preferred), or a fluorine, chlorine, bromine or iodine atom; and optionally in the 6-position by a fluorine, chlorine, bromine or iodine atom, and when $R^3$ is a substituted or unsubstituted imidazole or saturated heterocyclic group, pesticidally-acceptable acid addition salts thereof, which have valuable activity against arthropod, plant nematode, helminth and protozoan pests, more particularly by ingestion of the compound(s) of general formula (I) by the arthropods. When groups are optionally substituted by one or more halogen atoms it is to be understood that the halogen atoms may be the same or different in the case of substitution by more than one halogen atom.

By the term 'pesticidally acceptable acid addition salts' is meant acid addition salts the anions of which are known and accepted in the art as being suitable for the formation of salts of pesticidally active bases for agricultural or horticultural use.

When intended for application to vertebrates to combat infection or infestation by arthropods, helminths or protozoa, the acid addition salts used will be non-toxic. By the term 'non-toxic' is meant acid addition salts the anions of which are innocuous to the vertebrates at the doses administered and which do not vitiate the beneficial effects produced by the cation. Suitable acid addition salts of compounds of general formula (I) wherein the substituent represented by $R^3$ is an imidazole, or saturated heterocyclic group include salts with inorganic acids, for example hydrochlorides, sulphates, phosphates and nitrates, and salts with organic acids, for example acetic acid. It is to be understood that where reference is made in the present specification to the compounds of general formula (I), such reference is intended to include the pesticidally acceptable acid addition salts of compounds of general formula (I), where appropriate.

Compounds of general formula (I), processes for their preparation, compositions containing them and methods for their use constitute features of the present invention.

It is to be understood that the halogen atoms on the phenyl group $R^4$ may be the same or different. When groups are substituted by more than one halogen atom it is to be understood that the halogen atoms may be the same or different.

Compounds of general formula (I) wherein $R^4$ contains the trifluoromethyl or trifluoromethoxy group, and $R^2$ represents an optionally halogenated alkylsulphonyl/sulphinyl/thio group containing from 1 to 4 carbon atoms are preferred. Compounds of general formula (I) wherein $R^2$ represents a perhalogenated alkylsulphonyl/sulphinyl/thio group containing from 1 to 4 carbon atoms are more preferred. Trifluoromethylthio, trifluoromethylsulphinyl and trifluoromethanesulphonyl are especially preferred for $R^2$.

Compounds of general formula (I) with 2,6-dichloro-4-trifluoromethyl or 2,6-dichloro-4-trifluoromethoxy substitution of the phenyl group ($R^4$) are especially preferred.

Compounds of general formula (I) which are of particular interest are:
1. 3-Cyano-1-(2,6-dichloro-4-trifluoromethylphenyl)-5-pyrrol-1-yl-4-trifluoromethylthiopyrazole
2. 3-Cyano-1-(2,6-dichloro-4-trifluoromethylphenyl)-5-pyrrol-1-yl-4-trifluoromethylsulphinylpyrazole
3. 3-Cyano-1-(2,6-dichloro-4-trifluoromethylphenyl)-5-piperidino-4-trifluoromethylsulphonylpyrazole
4. 3-Cyano-1-(2,6-dichloro-4-trifluoromethylphenyl)-5-pyrrolidino-4-trifluoromethylsulphonylpyrazole
5. 3-Cyano-1-(2,6-dichloro-4-trifluoromethylphenyl)-5-morpholino-4-trifluoromethylsulphonylpyrazole
6. 3-Cyano-1-(2,6-dichloro-4-trifluoromethylphenyl)-5-imidazol-1-yl-4-trifluoromethylsulphonylpyrazole
7. 3-Cyano-1-(2,6-dichloro-4-trifluoromethylphenyl)-5-pyrrol-1-yl-4-methylsulphonylpyrazole
8. 5-Azido-3-cyano-1-(2,6-dichloro-4-trifluoromethylphenyl)-4-trifluoromethylsulphonylpyrazole
9. 5-Hydrazino-3-cyano-1-(2,6-dichloro-4-trifluoromethylphenyl)-4-trifluoromethylsulphonylpyrazole
10. 3-Cyano-1-(2,6-dichloro-4-trifluoromethylphenyl)-5-(1,2,4-triazol-1-yl)-4-trifluoromethylsulphonylpyrazole
11. 3-Cyano-1-(2,6-dichloro-4-trifluoromethylphenyl)-5-(2,5-dimethylpyrrol-1-yl)-4-trifluoromethylthiopyrazole
12. 3-Cyano-1-(2,6-dichloro-4-trifluoromethylphenyl)-5-pyrazol-1-yl-4-trifluoromethylsulphonylpyrazole The numbers 1 to 12 are assigned to the above compounds for identification and reference hereinafter.

In experiments on activity against arthropods carried out on representative compounds, the following results (wherein ppm indicates the concentration of the compound in parts per million of the test solution applied) have been obtained:

Test 1

One or more of the dilutions of the compounds to be tested were made in 50% aqueous acetone.

(a) Test species : *Plutella xylostella* (Diamond-back Moth).

Turnip leaf discs were set in agar in petri-dishes and infected with 10 2nd instar larvae. Four replicate dishes were assigned to each treatment and were sprayed under a Potter Tower with the appropriate test dilution. Four or five days after treatment the dishes were removed from the constant temperature (25° C.) room in which they had been held and the mean percentage mortalities of larvae were determined. These data were corrected against the mortalities in dishes treated with 50% aqueous acetone alone which served as controls.

According to the above method (a) an application of 100 ppm of the following compounds was effective against the larvae of *Plutella xylostella*, producing at least 60% mortality.

Compound 1, 2, 3, 4, 5, 6, 7, 8, 9, 10, 11, 12.

The compounds of general formula (I) can be prepared by the application or adaptation of known methods (i.e. methods heretofore used or described in the chemical literature).

It is to be understood that in the description of the following processes that the sequences for the introduction of the various groups on the pyrazole ring may be performed in a different order and that suitable protecting groups may be required as will be apparent to those skilled in the art: compounds of general formula (I) may be converted by known methods into other compounds of general formula (I).

Compounds of general formula (I) wherein $R^3$ represents a group Het, and $R^1$, $R^2$ and $R^4$ are as hereinbefore defined may be prepared by the reaction of a compound of general formula (II) wherein X represents a chlorine or bromine atom with a heterocyclic compound Het-H from which the groups within the definition of $R^3$ are derived. The reaction may be performed with the free bases or in the case of the less basic heterocyclic groups by reaction of their anions formed by addition of a base, preferably sodium hydride, and in an inert solvent preferably dioxan, tetrahydrofuran, N,N-dimethylformamide, dimethylsulphoxide or sulpholane, at a temperature from 25° C. to 150° C.

Compounds of general formula I wherein $R^3$ represents an optionally substituted pyrrol-1-yl, pyrazol-1-yl, 1,2,4-triazol-4-yl or 1,2,3-triazol-1-yl group may be prepared by reaction of a compound of the (i) general formula III with the corresponding 1,4-diketone, or an acetal or ketal derivative thereof, or with an optionally substituted 2,5-dimethoxytetrahydrofuran.

(ii) general formula IV with the corresponding 1,3-diketone, or an acetal or ketal derivative thereof (ii) general formula III with the corresponding diacylhydrazine.

(iv) general formula V with the corresponding alkyne.

The above processes (i), (ii) and (iii) may be performed in a suitable inert solvent e.g. toluene, dioxan, tetrahydrofuran, ethanol or acetic acid, and optionally in the presence of an acid catalyst, preferably p-toluenesulphonic acid and at temperatures from 25° C. to 150° C.

Process (iv) may be performed in suitable inert solvent e.g. toluene and at temperatures from 0° C. to 150° C.; or Alternatively enol ethers corresponding to the alkyne may be employed and the resulting triazoline heated or acid or base hydrolysed to a triazole.

Intermediate halides of general formula (II) may be obtained from 5-aminopyrazoles of formula (III) by reaction with a diazotising agent, preferably an alkyl nitrite e.g. tert-butyl nitrite in the presence of a suitable halogenating agent preferably bromoform or anhydrous copper chloride at temperatures from 0° C. to 100° C. and optionally in the presence of an inert solvent, preferably acetonitrile.

Intermediate 5-aminopyrazoles of formula (III) wherein $R^2$ represents an $R^5S$ group may be prepared by reacting an intermediate of general formula (VI) with a compound of general formula:

$$R^5-SCl \qquad (VII)$$

(wherein $R^5$ is as hereinbefore defined) in an inert organic solvent, preferably acetic acid, chloroform or dichloromethane, optionally in the presence of a base, preferably pyridine, and at temperatures from 0° to 60° C.

Compounds of general formula (III) wherein $R^2$ represents an $R^5S$ group and $R^1$ represents a chlorine, bromine, iodine or fluorine atom or a cyano or nitro group, may also be prepared by the reaction of corresponding 4-thiocyanatopyrazoles of general formula VIII wherein $R^6$ represents a chlorine, bromine, iodine or fluorine atom or a cyano or nitro group with an organometallic reagent such as a compound of general formula:

$$R^5-Mg-X^1 \qquad (IX)$$

wherein $R^5$ is as hereinbefore defined and $X^1$ represents a halogen atom in an inert solvent, such as diethyl ether or tetrahydrofuran, and at a temperature from $-78°$ C. to the reflux temperature of the reaction mixture or a compound of general formula:

$$R^7-C|C^-Li^+ \qquad (X)$$

wherein $R^7-C\equiv C^-$ corresponds to $R^5$ in (I), in an inert solvent, such as tetrahydrofuran or diethyl ether, at temperatures from $-78°$ C. to ambient.

Compounds of general formula (III) in which $R^2$ represents an $R^5S$ group wherein $R^5$ is other than a 1-alkenylthio or 1-alkynylthio group may also be prepared by reacting an intermediate of general formula (VIII) with a base preferably sodium hydroxide, or a reducing agent preferably sodium borohydride, in the presence of a reagent of general formula:

$$R^{5'}-X^2 \qquad (XI)$$

wherein $R^{5'}$ is as hereinbefore defined for $R^5$ with the exclusion of 1-alkenyl and 1-alkynyl and $X^2$ represents a halogen, preferably bromine or iodine, for example methyl iodide or propargyl bromide, or with a base preferably sodium hydroxide, in the presence of a reagent of general formula:

$$F_2C=C(Z)Z' \qquad (XII)$$

wherein Z represents a fluorine, chlorine or bromine atom and Z' is as hereinbefore defined for Z or represents the trifluoromethyl group in an inert organic or aqueous-organic solvent, such as methanol, ethanol or dioxan or mixtures of these solvents with water, the reaction being performed at a temperature from $-40°$ C. to the reflux temperature.

Compounds of general formula (III) wherein $R^5S$ is other than a 1-alkenylthio or 1-alkynylthio group may be prepared by reductive alkylation of disulphides of general formula (XIII) employing a reducing agent preferably sodium dithionite or sodium borohydride, in the presence of a base, preferably sodium hydroxide or sodium carbonate, and of a halide of general formula (XI), such as methyl iodide, in an inert organic or aqueous-organic solvent such as ethanol or a mixture of alcohol and water, at a temperature from ambient to reflux.

Compounds of general formula (III) in which $R^2$ represents an $R^5SO$ or $R^5SO_2$— group may be prepared by oxidation of the sulphur atoms of the corresponding alkylthio, alkenylthio or alkynylthio compounds of formula (III) wherein $R^2$ is a group $R^5S$ as defined above; the oxidation may be effected employing oxidants of the formula:

$$R^8\text{—O—O—H} \qquad (XIV)$$

wherein $R^8$ represents the hydrogen atom, or a trifluoroacetyl or preferably 3-chlorobenzoyl group in a solvent e.g. dichloromethane or chloroform or trifluoroacetic acid and at temperatures from 0° C. to 60° C., or with a reagent such as potassium hydrogen persulphate or potassium salt of Caro's acid in a solvent e.g. methanol and water, and at a temperature from −30° C. to 50° C.

Intermediate 4-thiocyanatopyrazoles of general formula (VIII) may be prepared by the reaction of a compound of general formula (VI) with a thiocyanating agent, such as alkali metal or ammonium salts of thiocyanic acid (e.g. NaSCN) and bromine, in an inert organic solvent, such as methanol, and at a temperature from 0° C. to 100° C.

Intermediate disulphides of general formula (XIII) may be prepared by the hydrolysis of thiocyanates of general formula VIII using hydrochloric acid in the presence of ethanol or by reduction with sodium borohydride in ethanol, both being at a temperature from ambient to reflux. Alternatively the thiocyanates may be converted into compounds of general formula (XIII) by treatment with base, preferably aqueous sodium hydroxide and preferably under phase-transfer conditions with chloroform as co-solvent and in the presence of a phase transfer catalyst e.g. triethyl- benzylammonium chloride and at a temperature from ambient to 60° C.

According to a feature of the present invention, azido-pyrazoles of general formula (V) may be prepared by the reaction of halides of formula (II) with an alkali metal azide e.g. $NaN_3$, in an inert solvent, preferably N,N-dimethylformamide, dimethylsulphoxide or sulpholane, and at a temperature from 25° C. to 150° C.

According to a feature of the present invention, hydrazino-pyrazoles of general formula (IV) may be prepared by the reaction of halides of formula (II) with hydrazine hydrate in a suitable inert solvent for example dioxan or dimethylsulphoxide, and at temperatures from 25° C. to 100° C.

According to a further feature of the present invention, the abovementioned azides of general formula (V) may be prepared by diazotisation of 5-amino-pyrazoles of formula (III) using a reagent such as nitrosylsulphuric acid in a suitable solvent, preferably acetic acid, at a temperature from 0° C. to 50° C., and subsequent treatment with an alkali metal azide, e.g. $NaN_3$.

According to a further feature of the present invention, the abovementioned hydrazines of general formula (IV) may also be prepared by diazotisation of 5-aminopyrazoles of formula (III) employing the same procedure but with subsequent treatment with a reducing agent, preferably stannous chloride in the presence of an acid, preferably hydrochloric acid, at a temperature from 0° C. to 100° C.

Compounds of general formula (III) wherein $R^1$ represents a chlorine, bromine or iodine atom or a cyano or nitro group may be prepared by the diazotisation of a intermediate of general formula (XV) using sodium nitrite in a mineral acid, for example a mixture of concentrated sulphuric acid and acetic acid, at a temperature from 0° to 60° C., and by subsequent reaction with a copper salt and a mineral acid or with an aqueous solution of potassium iodide (when $R^1$ represents an iodine atom) at a temperature from 0° to 100° C.; or with cuprous cyanide, or sodium nitrite in the presence of a copper salt in an inert solvent e.g. water at pH from 1 to 7 at 25° to 100° C. The diazotisation may alternatively be performed employing an alkyl nitrite e.g. tert-butyl nitrite in the presence of a suitable halogenating agent preferably bromoform or iodine or anhydrous cupric chloride at temperatures from 0° C. to 100° C., and optionally in the presence of an inert solvent, preferably acetonitrile or chloroform.

Compounds of general formula (III) wherein $R^1$ represents a fluorine atom may be prepared by diazotisation of the corresponding amine of general formula (XV) using for example a solution of sodium nitrite in sulphuric acid and in the presence of fluoroboric acid or its sodium salt and subsequent thermolysis or photolysis of the diazonium fluoroborate derivative by methods known per se.

Compounds of general formula (III) wherein $R^1$ represents a fluorine atom or a cyano group may be prepared by the reaction of a halide of general formula (III) wherein $R^1$ represents a chlorine or bromine atom with an alkali metal fluoride, preferably caesium fluoride, or with a metal cyanide preferably KCN under anhydrous conditions in an inert solvent, preferably sulpholane, and at a temperature from ambient to 150° C.

Compounds of general formula (III) wherein $R^1$ represents a nitro group, and $R^2$ is a group $R^5SO_2$ or $R^5SO$ may be prepared by the reaction of an intermediate of general formula (XV) with an oxidant, preferably trifluoroperacetic acid or m-chloroperbenzoic acid, in an inert solvent, preferably dichloromethane, at a temperature from 0° C. to the reflux temperature. In this process concomitant oxidation at sulphur may occur when $R^2$ is $R^5S$.

Compounds of general formula (III) wherein $R^1$ represents the cyano group may also be prepared by the dehydration of a compound of general formula (XVI). The compound of general formula (XVI) may be prepared by the reaction of a compound of general formula (XVII) with a chlorinating agent, preferably thionyl chloride at ambient to reflux temperature, followed by reaction of the intermediate acid chloride with ammonia to give an intermediate amide. The dehydration is generally effected by heating with a dehydrating agent e.g. phosphorus pentoxide or preferably phosphorus oxychloride at a temperature from 50° C. to 250° C.

Compounds of general formula (III) wherein $R^1$ represents a chlorine or fluorine atom and $R^2$ represents an $R^5SO_2$, $R^5SO$ or $R^5S$ group, may be prepared by the reaction of a compound of general formula (XIX) wherein $X^4$ and Y both represent chlorine atoms or both represent fluorine atoms, is reacted with a phenylhydrazine of general formula:

R⁴NHNH₂ (XX)

(wherein R⁴ is as hereinbefore defined) or an acid addition salt thereof, e.g. the hydrochloride, in an inert solvent, preferably ether or tetrahydrofuran, and optionally in the presence of a base, e.g. triethylamine or sodium acetate, and at a temperature from 0° to the reflux temperature of the solvent. When an acid addition salt of the compound of general formula (XX) is used, the reaction with the compound of general formula (XIX) is effected in the presence of an alkali metal, e.g. sodium or potassium, acetate, carbonate or bicarbonate.

Compounds of general formula (III) wherein R² represents an R⁵SO₂, R⁵SO or R⁵S group and R¹ represents the cyano group may be prepared by the reaction of a compound of general formula (XXI) wherein R⁹ represents a cyano group with a compound of general formula R²CH₂CN, preferably a molar equivalent thereof, generally in the presence of an anhydrous inert organic solvent, e.g. ethanol, and a molar equivalent of a base, e.g. sodium ethoxide, and at a temperature from 0° to 50° C.

Intermediate compounds of the general formula (XXI) wherein the R⁹ group represents a cyano group may be prepared by diazotisation of the aniline R⁴NH₂ (wherein R⁴ is as hereinbefore defined) generally with a solution of a molar equivalent of sodium nitrite in a mineral acid, e.g. a mixture of concentrated sulphuric acid and acetic acid, at a temperature from 0° to 60° C., and then reacting with a compound of formula CH₃COCH(Cl)CN [preparation described in J. Org. Chem 43 (20), 3822 (1978)]in the presence of an inert solvent, e.g. a mixture of water and ethanol, optionally buffered, e.g. with excess sodium acetate, and at a temperature from 0° to 50° C.

Intermediates of general formula (VI) wherein R¹ represents the cyano group may be prepared by diazotisation of the aniline R⁴NH₂ (wherein R⁴ is as hereinbefore defined) generally with a solution of a molar equivalent of sodium nitrite in a mineral acid, e.g. a mixture of concentrated sulphuric acid and acetic acid, at a temperature from 0° to 60° C., and then reacting with a compound of general formula:

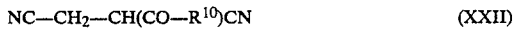

NC—CH₂—CH(CO—R¹⁰)CN (XXII)

wherein R¹⁰ represents an alkoxy group containing from 1 to 6 carbon atoms, preferably the ethoxy group, or a hydrogen atom in the presence of an inert solvent, e.g. a mixture of water and ethanol, and optionally buffered, e.g. with sodium acetate, and at a temperature from 0° to 50° C. Subsequent mild hydrolysis with a base such as aqueous sodium hydroxide, sodium carbonate or ammonia may be necessary to effect the cyclisation.

Intermediates of general formula (XXII) used above, in which R¹⁰ represents the hydrogen atom, may be employed as alkali metal enolate salts which are converted into the aldehydes under the acidic conditions of the above coupling reaction.

Intermediates of general formula (VI) in which R¹ is as defined may be prepared by decarboxylation of a compound of general formula (XXIII) wherein R¹ is as defined, generally performed by heating at a temperature from 100° C. to 250° C. optionally in the presence of an inert organic solvent, particularly N,N-dimethylaniline. Alternatively intermediates of general formula (VI), may be prepared directly from esters of general formula (XXIV), by heating in an inert organic solvent preferably acetic acid at a temperature from 50° C. to reflux, in the presence of a strong acid preferably hydrobromic acid. When the R¹ group within the definition of this process is a chlorine or fluorine atom concomitant halogen exchange may also occur to give intermediates wherein R¹ represents a bromine atom.

Intermediate carboxy compounds of general formula (XXIII) may be prepared by hydrolysis of esters of general formula (XXIV), preferably with an alkali metal hydroxide in a solvent such as an aqueous alcohol at a temperature from 0° C. to the reflux temperature of the reaction mixture.

Intermediate esters of general formula (XXIV) wherein R¹ represents a cyano group may be prepared from esters ROOCCH₂CN and intermediates of general formula (XXI) wherein R⁹ represents a cyano group.

Intermediate esters of general formula (XXIV) wherein R¹ represents a chlorine or fluorine atom may be prepared by the reaction of a phenylhydrazine (XX) with a compound of general formula (XXV) wherein X⁴, Y and R are as hereinbefore defined.

Alternatively intermediates corresponding to general formula (VI) in which R¹ represents a chlorine or fluorine atom, may be prepared by reaction of the corresponding 4-formylpyrazoles of general formula (XXVI) with an acid, preferably aqueous hydrochloric acid, in a solvent preferably ethanol at a temperature from 50° C. to the reflux temperature.

Intermediates of general formula (XXVI) may be prepared by reaction of nitriles of general formula (XXVII) with a suitable reducing agent, preferably diisobutyl aluminium hydride in an inert solvent, preferably tetrahydrofuran at a temperature from −78° C. to ambient temperature.

Intermediates of general formula (XXVII) may be prepared by the reaction of a compound of general formula (XXVIII) wherein X⁴ and Y are as hereinbefore defined (i.e. dichlorodicyanoethylene or difluorodicyanoethylene), with a phenylhydrazine (XX).

Intermediates of general formula (XXIX) wherein R¹¹ represents an R² group or a hydrogen atom may be prepared by performing a Curtius rearrangement of the acid azide of general formula (XXX) by heating in an inert organic solvent such as toluene at a temperature from 50° C. to 150° C. to give an isocyanate which is then reacted with, for example tert-butanol, to give a carbamate, which in turn is hydrolysed using dilute acid preferably hydrochloric acid in ethanol at a temperature from ambient to reflux.

Intermediate acid azides of general formula (XXX) may be prepared by reaction of a carboxylic acid of general formula (XVII) or (XXXI) with an azide transfer reagent such as diphenyl phosphoryl azide in the presence of a base, preferably triethylamine and in an inert solvent preferably N,N-dimethylformamide, and at a temperature from 0° to 60° C.

Intermediate carboxylic acids of general formulae (XVII) and (XXXI) may be prepared by hydrolysis of the corresponding esters of general formula (XVIII) and (XXXII), using a base such as sodium hydroxide and a solvent such as aqueous alcohol, and at a temperature from 0° C. to the reflux temperature of the solvent.

Intermediate carboxylic esters of general formulae (XXXII) may be prepared by reaction of an intermediate (XXXIII) wherein R and R² are as hereinbefore defined and $X^6$ is a leaving group, e.g. the chlorine atom, with a phenylhydrazine (XX).

Intermediate carboxylic esters of general formulae (XVIII) and (XXXII) may alternatively be prepared by the reaction of a compound (XXXIV) with a compound of general formula $R^{11}CH_2CN$ wherein $R^{11}$ is as hereinbefore defined.

Intermediates of general formula (XXXIV) may be prepared from known compounds (e.g. CH₃COCH(Cl)COOR) in a similar manner to that described above for compounds of general formula (XXI) wherein $R^9$ represents a cyano group.

Intermediate halides of general formula (XXXIII) wherein $X^6$ represents a chlorine atom and R and $R^2$ are as hereinbefore defined, may be prepared by the reaction of the sodium or potassium salts (XXXIII) wherein $X^6$ is $-O^-Na^+$ or $-O^-K^+$ with a suitable chlorinating agent, preferably phosphorus oxychloride, optionally in the presence of an inert solvent, e.g. tetrahydrofuran, and at a temperature from 0° C. to the reflux temperature of the solvent.

Intermediate salts (XXXIII) wherein $X^6$ is $-O^-Na^+$ or $-O^-K^+$ may be prepared by methods described in the literature, wherein active methylene compounds $R^2CH_2CN$ are reacted with dialkyl oxalates, e.g. diethyl oxalate, in the presence of a metal alkoxide, e.g. sodium ethoxide, in an inert solvent, e.g. an alcohol such as ethanol, and at a temperature from 25° C. to the reflux temperature of the solvent.

Intermediate diaminoesters corresponding to general formula (XXXV) may be prepared by reaction of an appropriately substituted phenylhydrazine of general formula (XX) with an alkali metal salt of an alkyl dicyanoacetate of general formula:

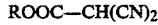
ROOC—CH(CN)₂     (XXXVI)

(wherein R is as hereinbefore defined) preferably potassium ethyl dicyanoacetate using hydrochloric acid, at ambient to reflux temperature. Alkyl dicyanoacetate potassium salts may be prepared by reaction of the appropriate alkyl chloroformate with malononitrile in the presence of potassium hydroxide in tetrahydrofuran at a temperature of 0° to 100° C.

Intermediate diaminosulphonylpyrazoles of general formula (XV) wherein $R^2$ represents a sulphonyl group $R^5SO_2$ may be prepared in a similar manner to the process just described by reaction of a phenylhydrazine (XX) with an alkali metal salt of a suitable alkylsulphonylmalononitrile of general formula:

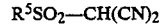
$R^5SO_2$—CH(CN)₂     (XXXVII)

(wherein $R^5$ is as hereinbefore defined).

The preparation of compounds of general formula (XXXVII) is described in the literature.

Intermediate esters of general formula (XXIV) in which $R^1$ represents a chlorine, bromine or fluorine atom or a nitro group, may be prepared via diazotisation of compounds of general formula (XXXV).

Intermediate esters of general formula (XXXII) may also be prepared from the reaction of a phenylhydrazine of general formula (XX) with an alkali metal salt of general formula (XXXVIII) wherein M is sodium or potassium and R is as hereinbefore defined. The reaction is performed in an acidic medium generally dilute sulphuric acid, optionally in the presence of a co-solvent e.g. ethanol, and at a temperature from ambient to the reflux temperature of the solvent.

Intermediates of general formula VI wherein $R^1$ represents a nitro group, may be prepared by the reaction of the corresponding diamine with an oxidant, preferably trifluoroperacetic acid or m-chloroperbenzoic acid in an inert solvent preferably dichloromethane at a temperature from 0° C. to reflux.

The following Examples and Reference Examples illustrate the preparation of compounds of general formula (I) according to the present invention:

EXAMPLE 1

Compound Nos 1, 2 and 7

To a solution of 5-amino-3-cyano-1-(2,6-dichloro-4-trifluoromethylphenyl)-4-trifluoromethylthiopyrazole (2.13 g) stirred in acetic acid (40 ml) was added 2,5-dimethoxytetrahydrofuran (2.0 g, 95%). The solution was heated under reflux for 5 hours, then evaporated in vacuo. The oily residue was dissolved in dichloromethane and washed in turn with water (1×50 ml), sodium bicarbonate solution (2×50 ml), and water (1×50 ml). The dichloromethane solution was dried over anhydrous magnesium sulphate, filtered, and evaporated in vacuo. The resultant oil (2.15 g) was purified by chromatography on silica (M&B, 40/60 flash silica, 0.7 kg cm²) eluting with dichloromethane/hexane (1:1). After evaporation 3-cyano-1-(2,6-dichloro-4-trifluoromethylphenyl)-5-pyrrol-1-yl-4-trifluoromethylthiopyrazole was obtained as colourless crystals (1.69 g), mp 97.4°–98.2° C.

By proceeding in a similar manner but replacing the 5-amino-3-cyano-1-(2,6-dichloro-4-trifluoromethylphenyl)-4-trifluoromethylthiopyrazole in the above example by 5-amino-3-cyano-1-(2,6-dichloro-4-trifluoromethylphenyl)-4-trifluoromethylsulphinylpyrazole, 3-cyano-1-(2,6-dichloro-4-trifluoromethylphenyl)-5-pyrrol-1-yl-4-trifluoromethylsulphinylpyrazole was obtained as a white solid, m.p. 165.4°–166.8° C.

By proceeding in a similar manner but replacing the 5-amino-3-cyano-1-(2,6-dichloro-4-trifluoromethylphenyl)-4-trifluoromethylthiopyrazole in the above example by 5-amino-3-cyano-1-(2,6-dichloro-4-trifluoromethylphenyl)-4-methylsulphonylpyrazole, 3-cyano-1-(2,6-dichloro-4-trifluoromethylphenyl)-4-methylsulphonyl-5-pyrrol-1-ylpyrazole was obtained as a white solid, mp 200.5°–201.5° C. The preparation of the starting material for this compound is described in European Patent Publication No. 234119.

Reference Example 1

5-Amino-3-cyano-1-(2,6-dichloro-4-trifluoromethylphenyl)-4-trifluoromethylsulphinylpyrazole used in the above Example was prepared as follows:

A stirred solution of 5-amino-3-cyano-1-(2,6-dichloro-4-trifluoromethylphenyl)-4-trifluoromethylthiopyrazole (10.0 g) in dichloromethane (100 ml) was treated with m-chloroperbenzoic acid (4.5 g). After stirring overnight additional m-chloroperbenzoic acid (1.6 g) was added in 2 portions, and left for 2 days.

The reaction product was diluted with ethyl acetare (30 ml) and then washed in turn with sodium sulphite solution (50 ml), sodium carbonate solution (50 ml) and with water (50 ml). After drying over magnesium sulphate, this was filtered and evaporated in vacuo. Purification by chromatography on silica (M&B, 40/60 flash silica, 0.7 kg cm²) eluting with dichloromethane gave the title compound as a white solid (6.0 g), m.p. 200.5°–201° C.

5-Amino-3-cyano-1-(2,6-dichloro-4-trifluoromethylphenyl)-4-trifluoromethylthiopyrazole used in the above Example was prepared as follows:

A solution of 5-amino-3-cyano-1-(2,6-dichloro-4-trifluoromethylphenyl)pyrazole (20.0 g) in dichloromethane (100 ml) was stirred magnetically and treated dropwise with a solution of trifluoromethylsulphenyl chloride (10.8 g) in dichloromethane (50 ml) during 1 hour. The solution was stirred overnight at room temperature, then washed with water (100 ml), dried over anhydrous magnesium sulphate, filtered, and evaporated in vacuo to give a solid (26.3 g). This was recrystallised (toluene/hexane) to give the title compound as fawn crystals (24.2 g) m.p. 169°–171° C. 5-Amino-3-cyano-1-(2,6-dichloro-4-trifluoromethylphenyl)pyrazole used above was prepared as follows:

A suspension of nitrosyl sulphuric acid prepared from sodium nitrite (7.0 g) and concentrated sulphuric acid (27.5 ml) was diluted with acetic acid (25 ml), cooled to 25° C., and stirred mechanically. To this was added a solution of 2,6-dichloro-4-trifluoromethylaniline (21.2 g) in acetic acid (50 ml) dropwise over 15 minutes at 25°–32° C. This mixture was heated to 55° C. for 20 minutes and poured onto a stirred solution of ethyl 2,3-dicyanopropionate (14.0 g) in acetic acid (60 ml) and water (125 ml) at 10°–20° C. After 15 minutes, water (200 ml) was added, and the oily layer separated. The aqueous solution was then extracted with dichloromethane (3×70 ml) and the extracts combined with the oil and washed with ammonia solution (to pH9). The organic phase was then stirred with ammonia (20 ml) for 2 hours, and the dichloromethane layer then separated. This was washed with water (1×100 ml), 1N hydrochloric acid (1×100 ml), dried over anhydrous magnesium sulphate, filtered, and evaporated in vacuo to give an oily solid. Crystallisation from toluene/hexane gave the title compound as brown crystals (20.9 g), m.p. 140°–142° C.

EXAMPLE 2

Compound Nos. 3, 4, 5 and 6

Piperidine (0.51 g) was added to a solution of 5-bromo-3-cyano-1-(2,6-dichloro-4-trifluoromethylphenyl)-4-trifluoromethylsulphonylpyrazole (1.5 g) in dioxan (15 ml). The mixture was heated at 60° C. for 3 hours, evaporated in vacuo, diluted with water (60 ml) and extracted with dichloromethane (2×50 ml). The extract was washed with dilute hydrochloric acid (1×50 ml), dried over anhydrous magnesium sulphate, filtered, and evaporated in vacuo to give a yellow solid (1.4 g). Recrystallisation from toluene/hexane gave 3-cyano-1-(2,6-dichloro-4-trifluoromethylphenyl)-5-piperidino-4-trifluoromethylsulphonylpyrazole as yellow crystals (0.87 g) m.p. 153°–155° C. By proceeding in a similar manner but replacing the piperidine by pyrrolidine, to gave 3-cyano-1-(2,6-dichloro-4-trifluoromethylphenyl)-5-pyrrolidino-4-trifluoromethylsulphonyl-pyrazole as a pale yellow solid, m.p. 187°–189° C.

By proceeding in a similar manner but replacing the piperidine by morpholine, to gave 3-cyano-1-(2,6-dichloro-4-trifluoromethylphenyl)-5-morpholino-4-trifluoromethylsulphonylpyrazole as a white solid, m.p. 167°–169° C.

By proceeding in a similar manner but replacing the piperidine by imidazole, to gave 3-cyano-1-(2,6-dichloro-4-trifluoromethylphenyl)-5-imidazol-1-yl-4-trifluoromethylsulphonylpyrazole as a white solid, m.p. 214°–215° C.

Reference Example 2

5-Bromo-3-cyano-1-(2,6-dichloro-4-trifluoromethylphenyl)-4-trifluoromethylsulphonylpyrazole used in the above Example was prepared as follows:

A suspension of 5-amino-3-cyano-1-(2,6-dichloro4-trifluoromethylphenyl)-4-trifluoromethylsulphonylpyrazole (43.8 g) was stirred in a mixture of bromoform (141 ml) and dry acetonitrile (63 ml). Tert-butyl nitrite (29.9 g) was added dropwise during 5 minutes, and the mixture heated at 60°–70° C. for 2.75 hours. After cooling to 25° C. a further addition of tert-butyl nitrite (29.9 g) was made, and the heating resumed for 2 hours. Evaporation in vacuo gave a yellow oily solid which was triturated with hexane and filtered off. Two recrystallisations from toluene/hexane gave the title compound as a yellow solid (34.0 g), m.p. 136°–137° C.

5-Amino-3-cyano-1-(2,6-dichloro-4-trifluoromethylphenyl)-4-trifluoromethylsulphonylpyrazole used above was prepared as follows:

A partial solution of 5-amino-3-cyano-1-(2,6-dichloro-4-trifluoromethylphenyl)-4-trifluoromethylthiopyrazole (48.0 g) in chloroform (600 ml) was stirred mechanically and treated with m-chloroperbenzoic acid (61.4 g). The mixture was stirred and heated under reflux in an atmosphere of nitrogen for 3.5 hours. After cooling, an additional amount of m-chloroperbenzoic acid (12.3 g) was added, and reflux continued for 1 hour. The cooled mixture was diluted with ethyl acetate (600 ml), washed with a solution of sodium metabisulphite (2×250 ml), then with sodium hydroxide solution (2×250 ml) and finally with water (1×500 ml). The organic layer was dried over anhydrous magnesium sulphate, filtered, and evaporated in vacuo to give a fawn solid. Recrystallisation from toluene/hexane/ethyl acetate gave the title compound as white crystals (37.0 g) m.p. 219°–221.5° C.

EXAMPLE 3

Compound 8

To a solution of 5-bromo-3-cyano-1-(2,6-dichloro-4-trifluoromethylphenyl)-4-trifluoromethylsulphonylpyrazole (2.0 g) in dimethylsulphoxide (20 ml) was added sodium azide (0.33 g). After stirring overnight at room temperature the mixture was poured onto water (100 ml) and extracted with dichloromethane (3×50 ml). The combined extracts were washed with water (1×100 ml), dried over anhydrous magnesium sulphate, and evaporated in vacuo to give a brown solid (2.5 g). Purification by medium pressure chromatography on silica, eluting with hexane/dichloromethane (2:1) gave the title compound as a white solid (1.27 g), m.p. 131°–132° C.

EXAMPLE 4

Compound 9

Hydrazine hydrate (0.34 g) was added to a solution of 5-bromo-3-cyano-1-(2,6-dichloro-4-trifluoromethylphenyl)-4-trifluoromethylsulphonylpyrazole (1.0 g) in dioxan (15 ml), and the mixture heated at 60° C. for 1½ hours. The pale yellow solution was decanted from a little solid and evaporated in vacuo. This was reevaporated after addition of toluene, and the residual oil purified by medium pressure chromatography on silica, eluting with dichloromethane. The resulting product was recrystallised from toluene/hexane to furnish the title compound as a white solid (0.7 g), m.p. 183°–184° C.

EXAMPLE 5

Compound 10

To a solution of 5-bromo-3-cyano-1-(2,6-dichloro-4-trifluoromethylphenyl)-4-trifluoromethylsulphonylpyrazole (2.0 g) in dioxan (30 ml) was added 1,2, 4-triazole (0.74 g), and the mixture heated under reflux overnight. After cooling to ambient temperature, sodium hydride (0.125 g) was added and the mixture heated under reflux for 2 days. The solvent was evaporated in vacuo and the residue dissolved in dichloromethane (50 ml) and washed with water (50 ml). The aqueous layer was re-extracted with dichloromethane (50 ml) and the combined organics dried over anhydrous magnesium sulphate, then evaporated in vacuo to give a yellow oil. Purification by chromatography on silica, eluting with dichloromethane/hexane (1:1) gave 3-cyano-1-(2,6-dichloro-4-trifluoromethylphenyl)-5-(1,2,4-triazol-1-yl)-4-trifluoromethylsulphonylpyrazole (0.3 g) as a white solid, m.p. 172.3°–173.7° C.

EXAMPLE 6

Compound 11

A mixture of 5-amino-3-cyano-1-(2,6-dichloro-4-trifluoromethylphenyl)-4-trifluoromethylthiopyrazole (8.0 g) and acetonylacetone (4.34 g) in toluene (250 ml) containing p-toluenesulphonic acid (0.5 g) was heated under reflux with a Dean and Stark take-off head fitted to the flask. After 31½ hours evaporation in vacuo gave a dark solid, which was dissolved in dichloromethane (100 ml) and washed in turn with water (100 ml) and saturated sodium carbonate solution (50 ml). The organic layer was dried over anhydrous magnesium sulphate, and evaporated in vacuo to give a dark semisolid. Purification by dry column chromatography (Kieselgel 60G) eluting with dichloromethane/hexane (1:3) gave 3-cyano-1-(2,6-dichloro-4-trifluoromethyl-phenyl)-5-(2,5-dimethylpyrrol-1-yl)-4-trifluoromethylthiopyrazole as a white solid (5.9 g), m.p. 142.3°–144° C.

EXAMPLE 7

Compound 12

A mixture of 3-cyano-1-(2,6-dichloro-4-trifluoromethylphenyl)-5-hydrazino-4-trifluoromethylsulphonylpyrazole (1.6 g), 1,1,3,3-tetramethoxypropane (0.58 g), ethanol (10 ml) and concentrated hydrochloric acid (1 ml) was heated under reflux for 4 hours. After evaporation in vacuo the residue was dissolved in dichloromethane (200 ml) and washed in turn with sodium bicarbonate solution (2×50 ml) and with water (50 ml). Filtration (phase separating paper), followed by evaporation gave a red solid, which was purified by chromatography on silica, eluting with dichloromethane/hexane (1:1). The product was recrystallised from toluene giving 3-cyano-1-(2,6-dichloro-4-trifluoromethylphenyl)-5-pyrazol-1-yl-4-trifluoromethylsulphonylpyrazole (0.6 g) as a white solid, m.p. 191°–193° C.

According to a feature of the present invention, there is provided a method for the control of arthropod, plant nematode, helminth or protozoan pests at a locus which comprises the treatment of the locus (e.g. by application or administration) with an effective amount of a compound of general formula (I), or a pesticidally acceptable salt thereof, wherein the various symbols are as hereinbefore defined. The compounds of general formula (I) may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fishes, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata* and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Musca spp., Hypoderma spp., Gasterophilus spp., Simulium spp.); Hemiptera (e.g. Triatoma spp.); Phthiraptera (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis. Haemonchus contortus, Trichostrongylus colubriformis, Nematodirus battus, Ostertagia circumcincta, Trichostrongylus axei*, Cooperia spp. and *Hymenolepis nana;* in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoma cruzi*, Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptotermes spp.; in agriculture, against adults, larvae and eggs of Lepidoptera (butterflies and moths), e.g. Heliothis spp. such as *Heliothis virescens* (tobacco budworm), *Heliothis armigera* and *Heliothis zea*, Spodoptera spp. such as *S.exempta, S.littoralis* (Egyptian cotton worm), *S.eridania* (southern army worm), *Mamestra configurata* (bertha army worm); Earias spp. e.g. *E.insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Spar-

*ganothis pilleriana* (grape berry moth), *Cydia pomonella* (codling moth), Archips spp. (fruit tree tortrix moths), *Plutella xylostella* (diamond back moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseudococcus spp., Helopeltis spp. (mosquito bugs), Lygus spp., Dysdercus spp., Oxycarenus spp., Nezara spp.; Hymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci;* Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphagotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry, horticulture either directly or by spreading bacterial, viral, mycoplasma or fungal diseases of the plants, root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The invention also provides a method for the control of arthropod or nematode pests of plants which comprises the application to the plants or to the medium in which they grow of an effective amount of a compound of general formula (I) or a pesticidally acceptable salt thereof.

For the control of arthropods and nematodes, the active compound is generally applied to the locus in which arthropod or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 1 g to 1000 g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula (I) may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of general formula (I) are of value in controlling pests which feed on parts of the plant remote from the point of application, e.g. leaf feeding insects are killed by the subject compounds applied to roots.

In addition the compounds may reduce attacks on the plant by means of antifeeding or repellent effects.

The compounds of general formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies.

The compounds of general formula (I) are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection.

Administration of a small amount of a compound of general formula (I) or a pesticidally acceptable salt thereof preferably by combination with poultry feed is effective in preventing or greatly reducing the incidence of coccidiosis. The compounds are effective against both the cecal form (caused by *E. tenella*) and the intestinal forms (principally caused by *E. acervulina, E. brunetti, E. maxima* and *E. necatrix*).

The compounds of general formula (I) also exert an inhibitory effect on the oocysts by greatly reducing the number and or the sporulation of those produced.

The compositions hereinafter described for topical application to man and animals and in the protection of stored products, household goods, property and areas of the general environment may, in general, alternatively be employed for application to growing crops and crop growing loci and as a seed dressing.

Suitable means of applying the compounds of general formula (I) include:

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their faeces; to growing crops as foliar sprays, dusts, granules, fogs and foams; also as suspensions of finely divided and encapsulated compounds of general formula (I); as soil and root treatments by liquid drenches, dusts, granules, smokes and foams; and as seed dressings by liquid slurries and dusts.

The compounds of general formula (I) may be applied to control arthropods, helminths or protozoa in compositions of any type known to the art suitable for internal or external administration to vertebrates or application for the control of arthropods in any premises or indoor or outdoor area, containing as active ingredient at least one compound of general formula (I) in association with one or more compatible diluents or adjuvants appropriate for the intended use. All such compositions may be prepared in any manner known to the art.

Compositions suitable for administration to vertebrates or man include preparations suitable for oral, parenteral, percutaneous, e.g. pour-on, or topical administration.

Compositions for oral administration comprise one or more of the compounds of general formula (I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more compounds of general formula (I) and a carrier or diluent which may include a food substance or some other substance to induce consumption by the arthropod.

Liquid compositions include water miscible concentrates, emulsifiable concentrates, flowable suspensions, wettable or soluble powders containing one or more compounds of general formula (I) which may be used to treat substrates or sites infested or liable to infestation by arthropods including premises, outdoor or indoor storage or processing areas, containers or equipment and standing or running water.

Solid homogenous or heterogenous compositions containing one or more compounds of general formula (I), for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solutions or dispersions suitable for spraying, fogging and low- or ultra-low volume spraying may also be used.

Suitable solid diluents which may be used in the preparation of compositions suitable for applying the compounds of general formula (I) include aluminium silicate, kieselguhr, corn husks, tricalcium phosphate, powdered cork, absorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the compound of general formula (I) in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octyl-phenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of general formula (I) may take the form of solutions, suspensions and emulsions of the compounds of general formula (I) optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of general formula (I) may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as apropriate e.g. benomyl, iprodione), bactericides, arthropod or vertebrate attractants or repellents or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control arthropod, plant nematode, helminth or protozoan pests usually contain from 0.00001% to 95%, more particularly from 0.0005% to 50%, by weight of one or more compounds of general formula (I) or of total active ingredients (that is to say the compound(s) of general formula (I) together with other substances toxic to arthropods and plant nematodes, anthelmintics, anticoccidials, synergists, trace elements or stabilisers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, more particularly from 0.001% to 10%, by weight of one or more compounds of general formula (I). For administration to animals orally or parenterally, including percutaneously solid and liquid compositions normally contain from 0.1% to 90% by weight of one or more compound of general formula (I). Medicated feedstuffs normally contain from 0.001% to 3% by weight of one or more compounds of general formula (I). Concentrates and supplements for mixing with feedstuffs normally contain from 5% to 90%, and preferably from 5% to 50%, by weight of one or more compounds of general formula (I). Mineral salt licks normally contain from 0.1% to 10% by weight of one or more compounds of general formula (I). Dusts and liquid compositions for application to livestock, persons, goods, premises or outdoor areas may contain 0.0001% to 15%, and more especially 0.005% to 2.0%, by weight of one or more compounds of general formula (I). Suitable concentrations in treated waters are between 0.0001 ppm and 20 ppm, and more especially 0.001 ppm to 5.0 ppm. of one or more compounds of general formula (I) and may also be used therapeutically in fish farming with appropriate exposure times. Edible baits may contain from 0.01% to 5% and preferably 0.01% to 1.0%, by weight of one or more compounds of general formula (I).

When administered to vertebrates parenterally, orally or by percutaneous or other means, the dosage of compounds of general formula (I) will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

The following Composition Examples illustrate compositions for use against arthropod, plant nematode, helminth or protozoan pests which comprise, as active ingredient, compounds of general formula (I). The compositions described in Composition Examples 1 to 6 can each be diluted in water to give a sprayable composition at concentrations suitable for use in the field.

COMPOSITION EXAMPLE 1

A water soluble concentrate was prepared from

| | |
|---|---|
| 3-Cyano-1-(2,6-dichloro-4-trifluoromethylphenyl)-5-pyrrol-1-yl-4-trifluoromethylthiopyrazole | 7% w/v |
| Ethylan BCP | 10% w/v |
| and N-methylpyrrolidone to | 100% by | volume by dissolving the Ethylan BCP in a portion of N-methylpyrrolidone, and then adding the active ingredient with heating and stirring until dissolved. The resulting solution was made up to volume by adding the remainder of the solvent.

COMPOSITION EXAMPLE 2

An emulsifiable concentrate was prepared from

| | |
|---|---|
| 3-Cyano-1-(2,6-dichloro-4-trifluoromethylphenyl)-5-pyrrol-1-yl-4-trifluoromethylthiopyrazole | 7% w/v |
| Soprophor BSU | 4% w/v |
| Arylan CA | 4% w/v |
| N-methylpyrrolidone | 50% w/v |
| and Solvesso 150 to | 100% by | volume by dissolving Soprophor BSU, Arylan CA and the active ingredient in N-methylpyrrolidone, and then adding Solvesso 150 to volume.

COMPOSITION EXAMPLE 3

A wettable powder was prepared from

| | |
|---|---|
| 3-Cyano-1-(2,6-dichloro-4-trifluoromethylphenyl)-5-pyrrol-1-yl-4-trifluoromethylthiopyrazole | 40% w/v |
| Arylan S | 2% w/v |
| Darvan No. 2 | 5% w/v |
| and Celite PF to | 100% by | weight by mixing the ingredients, and grinding the mixture in a hammer-mill to a particle size less than 50 microns.

COMPOSITION EXAMPLE 4

An aqueous flowable formulation was prepared from

| | |
|---|---|
| 3-Cyano-1-(2,6-dichloro-4-trifluoromethylphenyl)-5-pyrrol-1-yl-4-trifluoromethylthiopyrazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water to | 100% by | volume by intimately mixing the ingredients and grinding in a bead mill until the median particle size was less than 3 microns.

COMPOSITION EXAMPLE 5

An emulsifiable suspension concentrate was prepared from

| | |
|---|---|
| 3-Cyano-1-(2,6-dichloro-4-trifluoromethylphenyl)-5-pyrrol-1-yl-4-trifluoromethylthiopyrazole | 30% w/v |
| Ethylan BCP | 10% w/v |
| Bentone 38 | 0.5% w/v |
| and Solvesso 150 to | 100% by | volume by intimately mixing the ingredients and grinding in a bead mill until the median particle size was less than 3 microns.

COMPOSITION EXAMPLE 6

Water dispersible granules were prepared from

| | |
|---|---|
| 3-Cyano-1-(2,6-dichloro-4-trifluoromethylphenyl)-5-pyrrol-1-yl-4-trifluoromethylthiopyrazole | 30% w/v |
| Darvan No. 2 | 15% w/v |
| Arylan S | 8% w/v |
| and Celite PF to | 100% by | weight by mixing the ingredients, micronising in a fluid-energy mill, and then granulating in a rotating pelletiser by spraying on sufficient water (up to 10% w/w). The resulting granules were dried in a fluid-bed drier to remove excess water.

Descriptions of commercial ingredients used in the foregoing Composition Examples Ethylan BCP: nonylphenol ethylene oxide condensate
Soprophor BSU: condensate of tristyrylphenol and ethylene oxide
Arylan CA: 70% w/v solution of calcium dodecylbenzenesulphonate
Solvesso 150: light $C_{10}$-aromatic solvent
Arylan S: sodium dodecylbenzenesulphonate
Darvan: sodium lignosulphonate
Celite PF: synthetic magnesium silicate carrier
Sopropon T36: sodium salt of polycarboxylic acid
Rhodigel 23: polysaccharide xanthan gum
Bentone38: organic derivative of magnesium montmorillonite

COMPOSITION EXAMPLE 7

A dusting powder may be prepared by intimately mixing:

| | |
|---|---|
| 3-Cyano-1-(2,6-dichloro-4-trifluoromethylphenyl)-5-pyrrol-1-yl-4-trifluoromethylthiopyrazole | |
| Talc superfine | 1 to 10% w/w (weight/weight) to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

COMPOSITION EXAMPLE 8

An edible bait may be prepared by intimately mixing:

| | |
|---|---|
| 3-Cyano-1-2,6-dichloro-4-trifluoromethylphenyl)-5-pyrrol-1-yl-4-trifluoromethylthiopyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 9

A solution may be prepared containing:

| | |
|---|---|
| 3-Cyano-1-(2,6-dichloro-4-trifluoromethylphenyl)-5-pyrrol-1-yl-4-trifluoromethylthiopyrazole | |
| Dimethysulphoxide | 15% w/v (weight/volume) to 100% by volume | by dissolving the pyrazole derivative in a portion of the dimethyl- sulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 μm pore size), by parenteral injection, at a rate of application of from 1.2 to 12 ml of solution per 100 kg of animal body weight.

COMPOSITION EXAMPLE 10

A wettable powder may be formed from:

| | |
|---|---|
| 3-Cyano-1-(2,6-dichloro-4-trifluoromethylphenyl)-5-pyrrol-1-yl-4-trifluoromethylthiopyrazole | 50% w/w |
| Ethylan BCP (a nonylphenol/ethylene oxide condensate containing 9 moles of ethylene oxide per mol of phenol) | 5% w/w |
| Aerosil (silicon dioxide of microfine-particle size) | 5% w/w |
| Celite PF (synthetic magnesium silicate carrier | 40% w/w | by adsorbing the Ethylan BCP onto the Aerosil, mixing with the other ingredients and grinding the mixture in a hammer-mill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration as drinking water, to control the arthropods, helminths or protozoa.

COMPOSITION EXAMPLE 11

A slow release bolus may be formed from granules containing a density agent, binder, slow-release agent and 3-cyano-1-(2,6-dichloro-4-trifluoromethylphenyl)-5-pyrrol-1-yl-4-trifluoromethylthiopyrazole compound at varying percentage compositions. By compressing the mixture a bolus with a specific gravity of 2 or more can be formed and may be administered orally to ruminant domestic animals for retention within the reticulorumen to give a continual slow release of pyrazole compound over an extended period of time to control infestation of the ruminant domestic animals by arthropods, helminths or protozoa.

COMPOSITION EXAMPLE 12

A slow release composition may be prepared from:

| | |
|---|---|
| 3-Cyano-1-(2,6-dichloro-4-trifluoromethylphenyl) pyrrol-1-yl-4-trifluoromethylthiopyrazole | 0.5 to 25% w/w |
| polyvinylchloride base | to 100% w/w | by blending the polyvinylchloride base with the pyrazole compound and a suitable plasticiser, e.g. dioctyl phthalate, and melt-extruding or hot-moulding the homogenous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

Similar compositions may be prepared by replacing the 3-cyano-1-(2,6-dichloro-4-trifluoro- methylphenyl)-5-pyrrol-1-yl-4-trifluoromethylthiopyrazole in the Composition Examples by the appropriate quantity of any other compound of general formula (I).

(I)

(II)

(III)

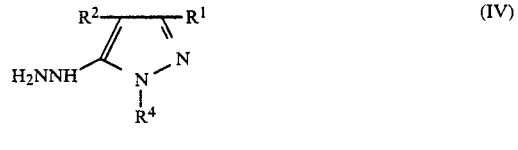

(IV)

(V)

(VI)

-continued

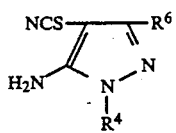 (VIII)

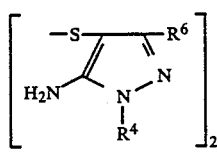 (XIII)

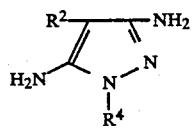 (XV)

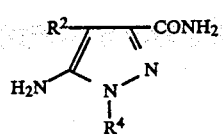 (XVI)

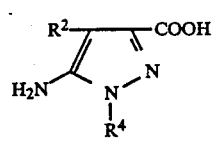 (XVII)

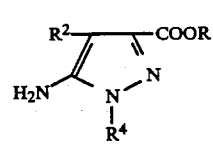 (XVIII)

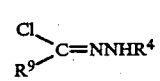 (XXI)

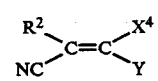 (XIX)

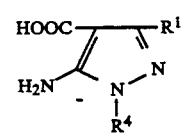 (XXIII)

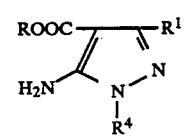 (XXIV)

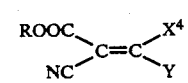 (XXV)

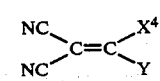 (XXVIII)

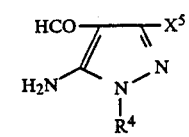 (XXVI)

-continued

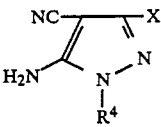 (XXVII)

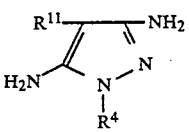 (XXIX)

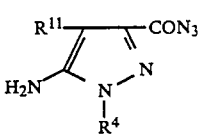 (XXX)

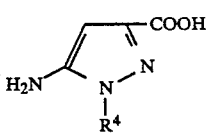 (XXXI)

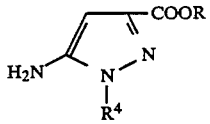 (XXXII)

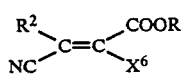 (XXXIII)

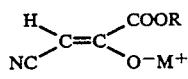 (XXXVIII)

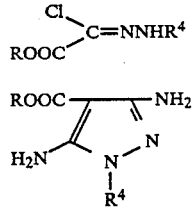 (XXXIV)

(XXXV)

We claim:
1. An N-phenylpyrazole derivative of the formula:

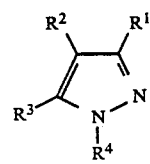 (I)

wherein $R^1$ represents a cyano group, $R^2$ represents a group $R^5SO_2$, $R^5SO$, or $R^5S$ in which $R^5$ represents a straight- or branched-chain alkyl, alkenyl or alkynyl group containing up to 4 carbon atoms which may be unsubstituted or substituted by one or more halogen atoms which may be the same or different; $R^3$ represents a group Het selected from pyrrol-1-yl, pyrazol-1-yl, imidazol-1-yl, 1,2,4-triazol-4-yl, 1,2,4-triazol-1-yl, 1,2,3-triazol-1-yl, 1,2,3-triazol-2-yl; and $R^4$ represents a phenyl group substituted in the 2-position by a fluorine, chlorine, bromine or iodine atom; in the 4-position by a straight- or branched-chain alkyl or alkoxy group containing from 1 to 4 carbon atoms which may be unsubstituted or substituted by one or more halogen atoms which may be the same or different, or a fluorine, chlorine, bromine or iodine atom; and unsubstituted or substituted in the 6-position by a fluorine, chlorine, bromine or iodine atom, or when $R^3$ is a substituted or unsubstituted imidazole heterocyclic group, a pesticidally-acceptable acid addition salt thereof.

2. A compound according to claim 1, wherein $R^4$ represents a phenyl group substituted in the 4-position by a trifluoromethyl or trifluoromethoxy group.

3. A compound according to claim 2, wherein $R^4$ represents 2,6-dichloro-4-trifluoromethylphenyl or 2,6-dichloro-4-trifluoromethoxyphenyl.

4. A compound according to claim 1 wherein $R^2$ represents an optionally halogenated alkylsulphonyl, alkylsulphinyl or alkylthio group containing from 1 to 4 carbon atoms.

5. A compound according to claim 4 wherein $R^2$ represents a perhalogenated alkylsulphonyl, alkylsulphinyl or alkylthio group.

6. A compound according to claim 5, wherein $R^2$ represents a trifluoromethylsulphonyl, trifluoromethylsulphinyl or trifluoromethylthio group.

7. A compound according to claim 1, which is 3-cyano-1-(2,6-dichloro-4-trifluoromethylphenyl)-5-pyrrol-1-yl-4-trifluoromethylthiopyrazole, 3-cyano-1-(2,6-dichloro-4-trifluoromethylphenyl)-5-pyrrol-1-yl-4-trifluoromethylsulphinylpyrazole, 3-cyano-1-(2,6-dichloro-4-trifluoromethylphenyl)-5-imidazol-1-yl-4-trifluoromethylsulphonylpyrazole, 3-cyano-1-(2,6-dichloro-4-trifluoromethylphenyl)-5-pyrrol-1-yl-4-methylsulphonylpyrazole, 3-cyano-1-(2,6-dichloro-4-trifluoromethylphenyl)-5-(1,2,4-triazol-1-yl)-4-trifluoromethylsulphonylpyrazole, 3-cyano-1-(2,6-dichloro-4-trifluoromethylphenyl)-5-(2,5-dimethylpyrrol-1-yl)-4-trifluoromethylthiopyrazole, 3-cyano-1-(2,6-dichloro-4-trifluoromethylphenyl)-5-pyrazol-1-yl-4-trifluoromethylsulphonylpyrazole or a pesticidally acceptable salt thereof.

8. An arthropodicidal, plant nematocidal, anthelmintic or anti-protozoal composition which comprises an N-phenylpyrazole derivative according to claim 1 or a pesticidally acceptable acid addition salt thereof in association with one or more compatible diluents or carriers.

9. A method for the control of arthropod, plant nematode, helminth or protozoal pests at a locus which comprises treatment of the locus with an N-phenylpyrazole derivative according to claim 1 or a pesticidally acceptable acid addition salt thereof.

* * * * *